(12) United States Patent
Helmus et al.

(10) Patent No.: US 7,709,439 B2
(45) Date of Patent: May 4, 2010

(54) BIOMATERIALS FOR ENHANCED HEALING

(75) Inventors: Michael N. Helmus, Worcester, MA (US); Robert Richard, Wrentham, MA (US); Melissa Dixon, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 503 days.

(21) Appl. No.: 10/781,932

(22) Filed: Feb. 20, 2004

(65) Prior Publication Data

US 2005/0187146 A1     Aug. 25, 2005

(51) Int. Cl.
  *A61K 38/00*   (2006.01)
  *C07K 14/00*   (2006.01)
  *A61F 2/02*    (2006.01)
  *A61F 13/00*   (2006.01)

(52) U.S. Cl. .................. 514/2; 530/300; 530/350; 424/422; 623/11.11

(58) Field of Classification Search .................. None
  See application file for complete search history.

(56) References Cited

U.S. PATENT DOCUMENTS

| | | | |
|---|---|---|---|
| 4,773,408 A * | 9/1988 | Cilento et al. ................. | 602/49 |
| 5,834,029 A   | 11/1998 | Bellamkonda et al. | |
| 5,955,578 A   | 9/1999 | Pierschbacher et al. | |
| 6,120,904 A   | 9/2000 | Hostettler et al. | |
| 6,197,325 B1  | 3/2001 | Macphee et al. | |
| 6,410,044 B1 * | 6/2002 | Chudzik et al. ............. | 424/423 |
| 6,991,652 B2 * | 1/2006 | Burg ............................. | 623/8 |
| 7,297,343 B2 * | 11/2007 | Zamora ...................... | 424/447 |
| 2003/0149173 A1 | 8/2003 | Rhee et al. | |
| 2004/0136977 A1 * | 7/2004 | Miyamoto ............... | 424/94.63 |

FOREIGN PATENT DOCUMENTS

| | | | |
|---|---|---|---|
| JP | 06128289 | * | 10/1992 |
| WO | WO 98/02189 A2 | | 1/1998 |

OTHER PUBLICATIONS

Kleinman et al., "Isolation and characterization of type IV procollagen, laminin, and heparan sulfate proteoglycan from the EHS sarcoma", Biochemistry 21: 6188-6193 (1982).*
Samuel et al., "Delivery of plasmid DNA to articular chondrocytes via novel collagen-glycosaminoglycan matrices", Human Gene Therapy 13: 791-802 (2002).*
International Search Report for International Patent Application No. PCT/US2005/005244, 5 pages.

* cited by examiner

*Primary Examiner*—Anand U Desai
(74) *Attorney, Agent, or Firm*—Mayer & Williams, P.C.; David B. Bonham

(57) ABSTRACT

The present invention relates to novel biomaterials and methods of using these new biomaterials to facilitate wound healing. The novel biomaterial may be a biocompatible polymer to which at least one bioactive polymer is covalently bonded by graft polymerization, copolymerization or cross-linking. Alternatively, the novel biomaterial may be a polymer blend comprising at least one biocompatible polymer and at least one bioactive polymer.

12 Claims, 1 Drawing Sheet

```
                            SEQUENCE LISTING

<160> NUMBER OF SEQ ID NOS: 22

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Tyr Arg Ala Arg Lys Gln Ala Ala Ser Ile Lys Val Ala Val Ser
 1               5                   10                  15

Ala Asp Arg

<210> SEQ ID NO 2
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 2

Cys Gly Arg Gly Asp Ser Pro Cys
  1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Phe Asp Ser
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Arg Gly Asp
  1

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Arg Gly Asp Ser
  1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Arg Gly Asp Ser Pro Lys
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Arg Gly Asp Thr Pro
  1               5
```

```
<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Asp Gly Arg Gly
  1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Penicillamine

<400> SEQUENCE: 9

Xaa Arg Gly Asp Cys
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Gly Asp Ser
  1

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Gly Asp Ser Pro Ala Ser Ser Lys Pro
  1               5                  10

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Gly Glu Ser
  1

<210> SEQ ID NO 13
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 13

Cys Asp Pro Gly Tyr Ile Gly Ser Arg
 1               5

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Ser Arg Ala Arg Lys Gln Ala Ala Ser Ile Lys Val Ala Val Ser
 1               5                  10                  15

Ala Asp Arg

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Arg Gly Asp Ser Pro
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Ile Gly Ser Arg
 1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg Arg Arg Gly Asp Ser Pro Lys
 1               5                  10

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

-continued

```
Ile Lys Val Ala Val
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Ile Ser Gly Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Val Lys Ala Val
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Arg Gly Asp Ser Pro Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Arg Gly Asp Gly Gly Gly
1               5
```

BIOMATERIALS FOR ENHANCED HEALING

TECHNICAL FIELD

The present invention relates to novel biomaterials and methods of using these new biomaterials to facilitate wound healing. The novel biomaterial may be a biocompatible polymer to which at least one bioactive polymer is covalently bonded by graft polymerization, copolymerization or cross-linking. Alternatively, the novel biomaterial may be a polymer blend comprising at least one biocompatible polymer and at least one bioactive polymer.

BACKGROUND

Wound healing begins almost immediately after injury, requiring the coordinated response by a variety of cells and the regulation of degradative and regenerative steps. The complexity of wound healing processes often leads to slow, inappropriate or lack of healing, often with serious medical consequences.

The extracellular matrix of mammalian tissue contains proteins known to support the attachment and promote the migration and differentiation of a wide variety of cells, such as fibronectin, vitronectin, collagens and laminin. When tissue is cut, burned or abraded, the extracellular matrix may be separated or lost. The matrix must be replaced before the wound can be completely repaired.

Accordingly, during wound healing, tissue is replaced by migration of cells into the wound and the subsequent synthesis of extracellular matrix by these cells. Typically, tissue structure and strength are derived by interactions of cells with the extracellular matrix, which is mediated by proteins such as fibronectin, vitronectin, collagen, laminin, etc. that are found in the matrix. The extracellular matrix, in addition to providing a scaffold for cell migration and attachment, also directs cell proliferation and differentiation.

Many analogues of extracellular matrix have been developed to promote wound healing (e.g., Dickerson et al., U.S. Pat. No. 5,677,276; Pierschbacher et al., U.S. Pat. No. 5,955,578; Clark et al., U.S. Pat. No. 6,194,378; Vuori et al., U.S. Pat. No. 5,677,276; McPhee et al., U.S. Pat. No. 6,197,325; Bellamkonda et al., U.S. Pat. No. 6,156,572; Bellamkonda et al., U.S. Pat. No. 5,834,029 and references contained therein). However, novel, optimized biomaterials that lead to rapid and complete wound healing by providing a scaffold for cell migration and attachment, binding or acting as a reservoir for endogenous growth factors are still needed. Also needed are biomaterials that are capable of directing cell proliferation and differentiation.

SUMMARY

The present invention satisfies this and other needs by providing new biomaterials and methods for using these new biomaterials to facilitate wound healing. The new biomaterial comprises at least one biocompatible polymer in combination with at least one bioactive polymer comprised of at least one peptide and/or protein and at least one polysaccharide and/or proteoglycan.

In one aspect, the present invention provides a biomaterial comprising a bioactive polymer comprised of at least one peptide and/or protein and at least one polysaccharide and/or proteoglycan and a biocompatible polymer. The bioactive polymer and the biocompatible polymer are covalently bonded together.

In another aspect, the present invention provides a biomaterial comprising a bioactive polymer comprised of at least one peptide and/or protein subunit and at least one polysaccharide and/or proteoglycan subunit copolymerized with a biocompatible polymer.

In still another aspect, the present invention provides a biomaterial comprising a bioactive polymer comprised of at least one peptide and/or protein subunit and at least one polysaccharide and/or proteoglycan subunit grafted to a biocompatible polymer.

In still another aspect, the present invention provides a biomaterial comprised of a biocompatible polymer, a polysaccharide and/or proteoglycan subunit and a peptide and/or protein subunit. The polysaccharide and/or proteoglycan subunit is grafted to the biocompatible polymer to form a new biocompatible polymer. Then the peptide and/or protein subunit is grafted to the new biocompatible polymer to form the biomaterial.

DETAILED DESCRIPTION

Figure 1:
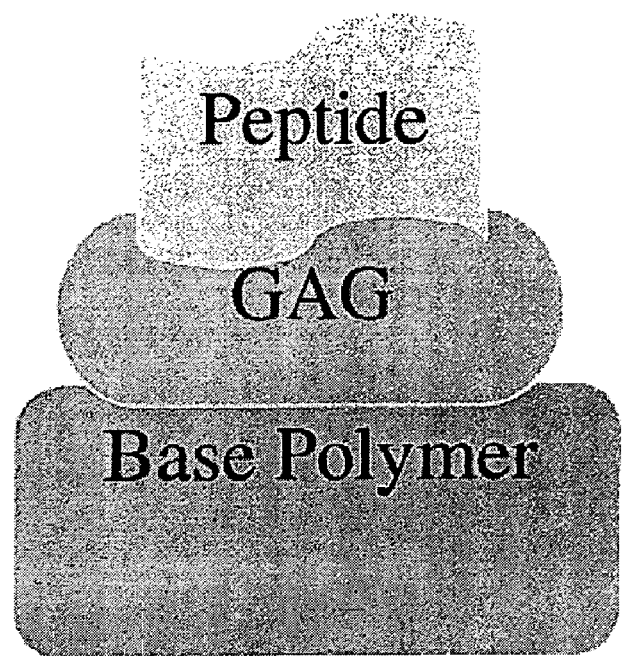
FIG. 1 is a schematic illustration of a polysaccharide and/or proteoglycan subunit grafted to a base polymer and a peptide or protein fragment grafted to the polysaccharide and/or proteoglycan subunit.

The present invention provides novel biomaterials that facilitate wound healing of many different types by providing cells with an attachment base for cell migration that also may bind or act as a reservoir for endogenous growth factors. The biomaterials are polymer blends, copolymers, graft polymers or interpenetrating polymer networks.

As used herein, the term "biocompatible polymer" refers to a compound that is biostable or biodegradable. A biocompatible polymer may be a homopolymer or a copolymer and may contain a reactive chemical functionality that allows for grafting. A biocompatible copolymer may contain both hydrophobic and hydrophilic portions and may be a synthetic polymer, derived from naturally occurring polymers, e.g., cellulose, collagen, gelatin, fibrin, chitosan, etc., or can be a naturally occurring polymer, e.g., cellulose, collagen, gelatin, fibrin, chitosan, etc. A biocompatible polymer may also be a bioactive polymer.

As used herein, the term "bioactive polymer" refers to a compound comprised of at least one peptide and/or protein subunit covalently bonded to at least one polysaccharide and/or proteoglycan subunit, unless otherwise specified. A bioactive polymer may be preformed before reacting or mixing with a biocompatible polymer to form a biomaterial. Alternatively, a biocompatible polymer may be mixed with either a polysaccharide and/or proteoglycan subunit or a peptide and/or protein subunit and the necessary subunit to form the biomaterial may be sequentially bonded to an intermediate polymer. In one embodiment, "bioactive polymer" refers to a compound consisting of least one peptide and/or protein subunit covalently bonded to at least one polysaccharide and/or proteoglycan subunit.

As used herein the term "polysaccharide and/or proteoglycan subunit" refers to a compound comprised of at least one polysaccharide and/or proteoglycan portion, unless otherwise specified. If the polysaccharide and/or proteoglycan subunit has more than one polysaccharide and/or proteoglycan portion, the polysaccharide and/or proteoglycan portion can be the same or different. In one embodiment, "polysaccharide and/or proteoglycan subunit" refers to a compound consisting of at least one polysaccharide and/or proteoglycan portion.

As used herein, the term "peptide and/or protein subunit" refers to a compound comprised of at least one peptide and/or protein portion, unless otherwise specified. If the peptide and/or protein subunit has more than one peptide and/or protein portion the peptide and/or protein portion can be the same or different. In one embodiment, the term "peptide and/or protein subunit" refers to a compound consisting of at least one peptide and/or protein portion, The present invention provides a biomaterial that is a combination of at least one biocompatible polymer and at least one bioactive polymer. The biocompatible polymer and a bioactive polymer may be covalently bonded to form a copolymer, a graft polymer or an interpenetrating polymer network or may be non-covalently associated to form a polymer blend (either, a miscible or immiscible blend).

Polysaccharide and/or proteoglycan subunits include, but are not limited to, aggrecan, agrin, bamacan, heparan sulfate, chondroitin sulfate, keratan sulfate, versican, CAT 301, phosphocan, perlecan, hyaluronan, decorin, dermatan sulfate, biglycan, fibromodulin, alginate, polylactate, polyglycolic acid, starch, dextran, agarose, chitan, chitosan and heparin. In one embodiment, the polysaccharide and/or proteoglycan subunit is perlecan, decorin or heparan sulfate. Preferably, the polysaccharide and/or proteoglycan subunit can sequester growth factors and/or enhance wound healing.

In some situations, the polysaccharide and/or proteoglycan subunit may be smaller fragments of the above subunits. For example, IdoA 2-O-sulfate and GlcN N-sulfate are essential for heparan sulfate and heparin binding to the growth factor FGF-2 and a decasaccharide or larger can stimulate mitogenic activity.

Polysaccharides and/or proteoglycans subunits used in the current invention may either be purchased from commercial sources or isolated from natural materials by methods known to the skilled artisan. For example, many proteoglycan subunits such as glycosoaminoglycans may be synthesized via fermentation processes.

An exemplary peptide and/or protein subunit is a cell adhesion peptide such as an RGD or a dRGD peptide. As used herein, the term "RGD peptide" refers to a peptide having at least one Arg-Gly-Asp-containing sequence with cell attachment promoting activity. A peptide containing the amino acid sequence "Y-Gly-Asp, wherein Y is D-Arg" (dRGD)" refers to a peptide having at least one Arg-Gly-Asp-containing sequence with cell attachment promoting activity. It is intended that the term "RGD peptide" in its broadest sense includes a peptide comprising Arg-Gly-Asp or a functional equivalent. For example, an amino acid such as lysine, ornithine, homoArginine (homoArg) or a mimic of these amino acids is a functional equivalent of arginine. Similarly mimics of Gly and Asp are functional equivalents of glycine and aspartic acid, respectively. Therefore, a peptide including, for example, Lys-Gly-Asp is considered an RGD peptide within the meaning of the present invention.

As used herein, the term "mimic" means an amino acid or an amino acid analog that has the same or similar functional characteristics as an amino acid. Thus, for example, an arginine analog can be a mimic of arginine if the analog contains a side chain having a positive charge at physiological pH, as is characteristic of the guanidinium side chain reactive group of arginine. A peptide mimetic or peptidomimetic is an organic molecule that retains similar peptide chain pharmacophore groups as are present in the corresponding peptide. Peptide mimetics also can be functional equivalents of Arg-Gly-Asp. Moreover, the peptide can be linear or cyclic. The peptides may be cyclized by procedures well known in the art, such as through a disulfide bridge or through a lactam bond.

As used herein, the term "amino acid" includes naturally occurring proteogenic amino acids and imino acids as well as non-naturally occurring amino acids and imino acids, analogs and mimics thereof. As used herein, the term "proteogenic" indicates that the amino acid can be incorporated into a protein in a cell through well-known metabolic pathways. In view of this broad definition of an amino acid, one of skill in the art would know that this definition includes, unless otherwise specifically indicated, naturally occurring proteogenic (L) amino acids, (D) amino acids, chemically modified amino acids including amino acid analogs, naturally occurring non-proteogenic amino acids such as norleucine and chemically synthesized compounds that have properties known in the art to be characteristic of an amino acid.

Peptide and/or protein subunits such as cell adhesion peptides may be derived from fibronectin, which provides a binding site for migrating cells coming in to replace cells lost due to injury in wound healing. Arg-Gly-Asp is also known as a cell attachment promoting sequence in a number of other adhesive proteins including, for example, vitronectin, collagen, fibrin and tenascin. Synthetic peptides containing the Arg-Gly-Asp sequence can promote cell attachment when presented as an insoluble substrate as well as inhibiting cell attachment to fibronectin or other adhesive proteins when in solution. Several receptors of this peptide sequence have been identified in various cell types (Pytela et al., *Cell* 1985, 191-198; Ruoslahti et al., *Science* 1987, 491-497). Depending on the type of cell to be attached, the Arg-Gly-Asp sequences may be modified to bind preferentially to individual receptors and therefore, can attract individual types of cells (Pierschbacher et al., *J. Biol. Chem.* 1987, 14080-14085). In addition, most extracellular matrix proteins contain a basic "heparin-binding" region, which appears to enhance adhesion and can be mimicked by polyarginine, polylysine or polyornithine or other basic residues. Moreover, the peptides can be linear or cyclic.

Accordingly, RGD peptides useful as peptide and/or protein subunits include, but are not limited to, R R R R R R G D S P K (SEQ ID NO: 17), G(dR) G D S P A S S K, nMe G (dR) (dR)(dR)(dR)(dR) G G G (Dr) G D S P A S S K wherein R is the amino acid arginine; (Arg), dR is the amino acid D-arginine (D-Arg), G is the amino acid glycine (Gly), D is the amino acid aspartic acid (Asp), S is the amino acid serine (Ser), P is the amino acid proline (Pro), K is the amino acid lysine (Lys), A is the amino acid alanine (Ala) and nMe is a N-methyl group.

Other RGD or dRGD peptides or proteins useful as peptide and/or protein subunits include, but are not limited to, 1-Adamantaneacetyl-Cys-Gly-Arg-Gly-Asp-Ser-Pro-Cys [Disulfide bridge: 1-8] (SEQ ID NO: 2), Arg-Phe-Asp-Ser (SEQ ID NO: 3), Fibronectin Adhesion-promoting Peptide, Fibronectin Fragment 1377-1388, Fibronectin Fragment 1977-1991, Fibronectin Fragment III1-C recombinant expressed in *Escherichia coli*, Fibronectin Proteolytic Fragment human plasma, Fibronectin Proteolytic Grament human plasma, Fibronectin Proteolytic Grament human plasma, Fibronectin Type III Connecting Segment Fragment 90-109, Fibronectin Type III Connecting Segment Fragment 1-25, Gly-Arg-Gly-Asp (SEQ ID NO: 4), Gly-Arg-Gly-Asp-Ser (SEQ ID NO: 5), Gly-Arg-Gly-Asp-Ser-Pro-Lys (SEQ ID NO: 6), Gly-Arg-Gly-Asp-Thr-Pro (SEQ ID NO: 7), Ser-Asp-Gly-Arg-Gly (SEQ ID NO: 8), N-Acetyl-Pen-Arg-Gly-Asp-Cys [Disulfide bridge: 1-5] (SEQ ID NO: 9), Arg-Gly-Asp, Arg-Gly-Asp-Ser (SEQ ID NO: 10), Arg-Gly-Asp-Ser-Pro-Ala-Ser-Ser-Lys-Pro (SEQ ID NO: 11), Arg-Gly-Glu-Ser (SEQ ID NO: 12) acetate salt, Cys-Asp-Pro-Gly-Tyr-Ile-Gly-Ser-Arg (SEQ ID NO: 13) and Cys-Ser-Arg-Ala-Arg-Lys-Gln-Ala-Ala-Ser-Ile-Lys-Val-Ala-Val-Ser-Ala-Asp-Arg (SEQ ID NO: 14). The above peptides are available from commercial suppliers Some other RGD components useful as peptide and/or protein subunits in the present invention include, for example, Peptite 2000 from Telios Pharmaceuticals and GRGDSP (SEQ ID NO: 15) (Tweden et al., *J. Heart Valve Dis.* 1995, (Suppl. I): S90-97; Lateff et al., *Biomaterials* 2002, 3159-3168).

YIGSR peptides (literal sequence disclosed as SEQ ID NO: 16) (e.g., Yamada et al., U.S. Pat. No. 5,039,885; Graf et al., *Biochemistry* 1987, 26, 6896) are also useful as peptide and/or protein subunits in the present invention. Exemplary YIGSR peptides (literal sequence disclosed as SEQ ID NO: 16) include, but are not limited to, Cys-Asp-Pro-Gly-Tyr-Ile-Gly-Ser-Arg (CDPGYIGSR) (SEQ ID NO: 13) and pentapeptide Tyr-Ile-Gly-Ser-Arg (YIGSR) (SEQ ID NO: 16) (Massia et al., *J Biol. Chem.* 1993, 8053-9). Covalently immobilized laminin peptide Tyr-Ile-Gly-Ser-Arg (YIGSR) (SEQ ID NO: 16) supports cell spreading and co-localization of the 67-kilodalton laminin receptor with alpha-actinin and vinculin.

IKVAV peptides (literal sequence disclosed as SEQ ID NO: 18) (e.g., Tashiro et al., *J. Biol. Chem.* 1989, 264, 16174; Jucker et al., *J. Neurosci. Res.* 1987, 26, 6896) are also useful as a peptide and/or protein subunit in the present invention. A preferred IKVAV (literal sequence disclosed as SEQ ID NO: 18) peptide is CYRARKQAASIKVAVSADR (SEQ ID NO:1) (Bellamkonda, U.S. Pat. No. 5,834,029).

The above peptides can be produced synthetically, recombinantly or derived from naturally occurring proteins, such as fibronectin, vitronectin, laminin, etc. Preferably, the peptides are made synthetically. Standard procedures for preparing synthetic peptides are well known in the art (M. Bodanszky, *Principles of Peptide Synthesis,* Springer-Verlag, New York, 1984; M. Bodanszky, *Peptide Chemistry,* $1^{st}$ and $2^{nd}$ eds., Springer-Verlag, New York, 1988 & 1993); and *Solid Phase Peptide Synthesis,* (available from Pierce Chemical Co.)).

In some situations, it may be desirable to use a cell adhesion protein or a fragment of a cell adhesion protein as a peptide and/or protein subunit in the present invention. Representative cell adhesion proteins include, but are not limited to, fibronectin, vitronectin, laminin, fibrin, tenascin and collagen. Cell adhesion proteins or fragments thereof may be obtained by synthetic or recombinant production, from commercial sources or other procedures known to the skilled artisan.

Another peptide and/or protein subunit that may used in the current invention is a growth factor protein such as, for example, insulin, insulin like growth factors, interleukin-4, platelet derived growth factor, TGF-β, EGF, NGF, IL-2, IL-3, GM-CSF, M-CSF, G-CSF, EPO, VEGF, FGF or biologically active analogs thereof. Preferred growth factors include VEGF, FGF and EGF. Growth factor proteins may be obtained by synthetic or recombinant production, from commercial sources or by procedures known to the skilled artisan.

Still another peptide and/or protein subunit which may used in the current invention is a synthetic growth factor mimetic such as those available from BioSET, Inc, College Park, Md. Growth factor mimetics may also be fragments of growth factor protein such as, for example, insulin, insulin like growth factors, interleukin-4, platelet derived growth factor, TGF-β, EGF, NGF, IL-2, IL-3, GM-CSF, M-CSF, G-CSF, EPO, FGF, VEGF or biologically active analogs thereof.

Still other peptide and/or protein subunits useful in the current invention are antimicrobial peptides such as, for example, magainins, protegrins, etc.

In some embodiments, a peptide and/or protein subunit used in the biomaterial of the invention may be comprised of more than one peptide or protein subunit. Thus, for example, the peptide and/or protein subunit may have both RGD peptide fragments and EGF peptide fragments. Similarly, a polysaccharide and/or proteoglycan subunit used in the biomaterial of the invention may be comprised of more than one polysaccharide or proteoglycan (e.g., perlecan and heparin). Finally, a bioactive polymer may be comprised of more than one peptide or protein and more than one polysaccharide or proteoglycan subunit (e.g., perlecan, heparin, RGD peptide fragments and EGF peptide fragments).

Bioactive polymers useful in practicing the current invention, include, but are not limited to, polymers where the peptide and/or protein subunit is an RGD peptide, IKVAV peptide (SEQ ID NO: 18), YISGR peptide (SEQ ID NO: 19), fibrin fragment or VEGF fragment. Also useful are polymers where the polysaccharide and/or proteoglycan subunit is heparan sulfate, chrondroitan sulfate, keratan sulfate, perlecan or heparin. Other useful bioactive polymers include, but are not limited to, polymers where the peptide and/or protein subunit is an RGD peptide, IKVAV peptide (SEQ ID NO: 18), YISGR peptide (SEQ ID NO: 19), fibrin fragment or VEGF fragment and the polysaccharide and/or proteoglycan subunit is heparan sulfate, chrondroitan sulfate, keratan sulfate, perlecan or heparin. Particularly useful bioactive polymers include, but are not limited to, polymers comprised of heparin sulfate and a RGD peptide, chrondroitan sulfate and a YISGR peptide (SEQ ID NO: 19), keratan sulfate and a VEGF fragment, a IKVAV peptide (SEQ ID NO: 18) and perlecan or heparin and a fibrin fragment.

Generally, polymers which are compatible with vascular tissue (i.e., biocompatible polymers) are useful in the present invention. For example, homopolymers and copolymers derived from monomers such as isobutylene, butyl acrylate and butyl methacrylate demonstrate exceptional vascular compatibility. Other polymers which are compatible with vascular tissue and may be used in the present invention have been described in U.S. Patent Publication 2005/0238684 entitled "Implantable or Insertable Medical Articles Having Covalently Modified, Biocompatible Surfaces," assigned to Boston Scientific Corporation, Natick, Mass. Polymers compatible with vascular tissue may also be copolymerized with a hydrogel like material such as, for example, PEG. Furthermore, reactive groups such as primary amines, e.g., aminoethyl methacrylate or other amino alkyl methacrylates, e.g., aminopropyl, aminopentyl, aminohexyl and aminoundecyl methacrylate may be attached to polymers compatible with vascular tissue (Guerts et. al., J. Applied Polymer Science 2001, 1401-1415).

In one embodiment, biocompatible polymers, include but are not limited to, isobutylene based copolymers of isobutylene and at least one other repeating unit (e.g., butyl acrylate, butyl methacrylate, substituted styrenes (e.g., amino styrenes, hydroxy styrenes, carboxy styrenes, sulfonated stryenes, etc.) homopolymers of polyvinyl alcohol, copolymers of polyvinyl alcohol and least one other repeating unit such as vinyl cyclohexyl ether, hydroxyethyl methacrylates, hydroxyl or amine terminated polyethylene glycols, etc.), acrylate based copolymers (e.g., methacrylic acid, methacrylamide, hydroxymethyl methacrylates, etc.), ethylene vinyl alcohol copolymers, acrylate based block, graft, gradient, statistical or random copolymers, silicone based copolymers of an aryl or alkyl siloxane and at least one repeated unit (e.g., butyl acrylate, butyl methacrylate, substituted styrenes (e.g., amino styrenes, hydroxy styrenes, carboxy styrenes, sulfonated stryenes, etc.) homopolymers of polyvinyl alcohol, copolymers of polyvinyl alcohol and least one other repeating unit, such as vinyl cyclohexyl ether, hydroxymethyl methacrylates, hydroxyl or amine terminated polyethylene glycols, etc.).

Biocompatible polymers may be, for example, a homopolymer or a copolymer (including alternating, random and block copolymers), a cyclic, linear or branched polymer (e.g., polymers with star, comb or dendritic architecture), a natural or synthetic polymer, a thermoplastic or thermosetting polymer. Biocompatible polymers include, but are not limited to, polycarboxylic acid polymers and copolymers including polyacrylic acids; acetal polymers and copolymers, acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including Nylon 66, polycaprolactams and polyacrylamides; resins including alkyl resins, phenolic resins, urea resins, melamine resins, epoxy resins, allyl resins and epoxide resins; polycarbonates; polyacrylonitriles; polyvinylpyrrolidones (cross-linked and otherwise), polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6.6-dimethyl-1,4-dioxan-2-one (a copolymer of polylactic acid and polycaprolactone is one specific example); polyether polymers and copolymers including polyaryl ethers such as polyphenylene ethers, polyether ketones, polyether ether ketones; polyphenylene sulfides; polyisocyanates; polyolefin polymers and copolymers, including polyalkylenes such as polyproylenes, polyethylenes (low and high density, low, and high molecular weight), polybutylenes (such as polybut-1-ene and polyisobutylene), poly-4-methylpen-1-enes, ethylene-alpha-olefin copolymers, ethylene-methyl-methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Elastomeric polymers are also useful biocompatible polymers. Among the preferred elastomeric polymers are (a) polyolefin polymers, for example, butyl-containing polymers such as polyisobutylene; (b) polyolefin copolymers, for example, polyolefin-polyvinylaromatic copolymers such as polyisobutylene-polystyrene copolymers, poly(butadiene/butylene)-polystyrene copolymers and polybutadiene-polystyrene copolymers; (c) silicone polymers and copolymers; and (d) acrylic acid polymers and copolymers; as well as blends thereof. Specific examples of polyolefin-polyvinylaromatic copolymers include polyolefin-polyvinylaromatic diblock copolymers and polyvinylaromatic-polyolefin-polyvinylaromatic triblock copolymers, such as a polystyrene-polyethylene/butylene-polystyrene (SEBS) triblock copolymer, available as Kraton®, and polystyrene-polyisobutylene-polystyrene (SIBS) triblock copolymers which are described, for example, in U.S. Pat. Nos. 5,741,331, 4,946,899 and 6,545,097. Additional polyolefin-polyvinylaromatic copolymers are set forth in the prior paragraph.

Biocompatible polymers may be biostable synthetic polymers such as, for example, polyurethane (including polycarbonate urethanes), isobutylene, polystyrene-isobutylene-polystyrene, silicone (e.g., polysiloxane and substituted polysiloxane), a thermoplastic elastomer, an ethylene vinyl acetate copolymer, a polyolefin elastomer, EPDM ethylene-propylene terpolymer rubber, polyamide elastomer, hydrogel or combinations thereof (Hostettler et al., U.S. Pat. No. 6,120,904; Hostettler et al., U.S. Pat. No. 6,265,016; Hostettler et al., U.S. Pat. No. 5,662,960; Hostettler et al., U.S. Pat. No. 5,576,072; Hostettler et al., U.S. Pat. No. 5,849,368; Hostettler et al., U.S. Pat. No. 5,919,570). Hydrogel polymers include, but are not limited to, derivatives of 2-hydroxyethylmethacrylate, polyvinyl alcohol, polyethylene oxide, polyethylene glycol, polyurethane hydrogel, naturally occurring hydrogels, e.g., gelatin, hyaluronic acid, cross-linked albumin, etc. or combinations thereof.

The biocompatible, biostable synthetic polymers described above may provide a permanent substrate or scaffold for cells and tissue growth. The mechanical properties of the biostable scaffold may determine the properties of the final tissue. Applications may include vascular prostheses and myocardial tissue scaffolds for tissue engineering applications to replace damaged cardiac tissue.

Biocompatible polymers that are biodegradable may also be used to provide a substrate or scaffold for tissue engineered constructs. Biocompatible polymers that are biodegradable include, but are not limited to, polyamides, polyorthoesters, polyanhydrides (PAN), polycaprolactone (PCL), maleic anhydride copolymers, polyhydroxybutyrate copolymers, as well as mixtures and blends thereof. Examples of the above include, but are not limited to, poly 1,3-(bis(p-carbophenoxy)

propane anhydride ((pCPP) an aromatic polyanhydride), polymer formed from the copolymerization of pCPP with sebacic acid (i.e., a copolymer of an aromatic diacid and an aliphatic diacid) and polyterephthalic acid (i.e., polyterephthalic anhydride, and aromatic anhydride), poly(L-lactide) (PLLA), poly(D,L-lactide), (PLA), polyglycolide(PGA), poly(L-lactide-co-D,L-lactide) (PLLA/PLA), poly(L-lactide-co-glycolide)PLLA/PGA), Poly(D,L-lactide-co-glycolide)(PLA/PGA), poly(glycolide-co-trimethylene carbonate) (PGA/PTMC), polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), poly(D,L-lactide-co-caprolactone) (PLA/PCL), poly(glycolide-co-caprolactone) (PGA/PCL), poly(phosphate ester), poly(amino acid) and poly(hydroxybutyrate), polydepsidpeptides, maleic anhydride copolymers, polyphosphazenes, polyiminocarbonates, poly[97.5% dimethyl-trimethylene carbonate)-co-(2.5% trimethlyene carbonate)], cyanacrylate, polyethylene oxide, hydroxypropylmethylcellulose, polysaccharides such as hyaluronic acid, chitosan and regenerate cellulose and proteins such as gelatin and collagen, among others.

The use of a bioactive polymer that is biodegradable at the same or similar rate as a biodegradable, biocompatible polymer may result in an temporary scaffold that promotes tissue neogenesis. Polymer blends, interpenetrating polymer networks, copolymers and graft polymers comprised of a biocompatible polymer that is biodegradable and a bioactive polymer are also expected to be biodegradable. Biodegradation can either occur at the same rate as new tissue formation or after wound healing is complete.

Biocompatible polymers particularly useful in forming the biomaterials of the invention include, but are not limited to, isobutylene based copolymers of isobutylene and at least one other repeating unit (e.g., butyl acrylate, butyl methacrylate, substituted styrenes (e.g., amino styrenes, hydroxy styrenes, carboxy styrenes, sulfonated stryenes, etc.) homopolymers of polyvinyl alcohol, copolymers of polyvinyl alcohol and least one other repeating unit, such as a vinyl cyclohexyl ether, hydroxymethyl methacrylates, hydroxyl or amine terminated polyethylene glycols, etc.), acrylate based copolymers (e.g., methacrylic acid, methacrylamide, hydroxymethyl methacrylates, etc.), ethylene vinyl alcohol copolymers, silicone based copolymers of an aryl or alkyl siloxane and at least one repeated unit (e.g., butyl acrylate, butyl polymer, (e.g., a copolymer of butyl methacrylate and PEG).

The bioactive and biocompatible polymers may be combined non-covalently to form polymer blends and covalently to form interpenetrating polymer networks, copolymers and graft polymers. Preferred combinations of bioactive and biocompatible polymers include, but are not limited to, polyurethanes, heparan sulfate and RGD peptides, polyethylene oxides, chrondroitin sulfate and YIGSR peptides (literal sequence disclosed as SEQ ID NO: 16), silicone polymers, keratan sulfate and VEGF biomimetic peptides, SIBS, perlecan and IKVAV peptides (literal sequence disclosed as SEQ ID NO: 18) and N-butyl methacrylate, heparin and fibrin fragments.

In one embodiment, a vascular compatible polymer (e.g., poly(ethylene glycol diacrylate) is polymerized with hyaluron to provide an interpenetrating network polymer. In another embodiment, a RGD peptide is grafted to poly(ethylene glycol diacrylate) which is then polymerized with hyaluron to provide an interpenetrating polymer network. Alternatively, a vascular compatible polymer such as poly (ethylene glycol diacrylate) may be polymerized with hyaluron which is grafted to a RGD peptide to provide an interpenetrating polymer network. Multifunctional polyisobutylene homo or copolymers which are endfunctionalized with a minimum of two reactive species (e.g., vinyl allyl, methacrylate, isocynate, amine, hydroxy, etc.) may also be polymerized with hyaluron grafted to a RGD peptide to provide another interpenetrating polymer network.

In one embodiment, a graft polymer is comprised of hyaluronic acid grafted to a copolymer of N-butyl methacrylate and glycidyl methacrylate. In another embodiment, the graft polymer is comprised of an RGD peptide grafted to a copolymer of N-butyl methacrylate and glycidyl methacrylate. In still another embodiment, the graft polymer is comprised of an RGD peptide and hyaluronic acid grafted to a copolymer of N-butyl methacrylate and glycidyl methacrylate. Those of skill in the art will appreciate that a number of bioactive polymers, biocompatible polymers, RGD peptides, peptide and/or protein fragments, IVKAV peptides (literal sequence disclosed as SEQ ID NO: 20), polysaccharides, polysaccharide fragments, etc. may be used to form graft polymers of the current invention.

Graft polymers may be prepared by attaching the grafting agent to a preformed polymer. Thus, RGD peptides, peptide and/or protein fragments, IVKAV peptides (literal sequence disclosed as SEQ ID NO: 20), polysaccharide, polysaccharide fragment, etc. may be attached to a preformed polymer by a variety of methods that will depend on the precise nature of the polymer and the grafting agent. For example, a polysaccharide or a peptide and/or protein fragment may be attached a carboxylic acid containing polymer by a variety of conventional methods, well known to those of skill in the art, used to form esters or amides.

Peptide and/or protein subunits and polysaccharide and/or proteoglycan polymer subunits may be joined by a number of procedures known to those of skill in the art to provide bioactive polymers. In one embodiment, cross-linking/coupling agents that include, but are not limited to, 1-ethyl-3-3-dimethylaminoproplylcarodiimide (EDC), dicyclohexyl-carbodiimide (DCC), glutaraldehyde, cyanogen bromide, N-hydroxysuccinimide, etc., are used to form bioactive polymers.

In some embodiments the peptide and/or protein subunit and polysaccharide and/or proteoglycan subunit can be covalently joined prior to incorporation of the biocompatible polymer in a blend, interpenetrating polymer network, copolymer or graft copolymer. The peptide and/or protein subunit and polysaccharide and/or proteoglycan subunit can be linked by the methods listed above.

In other embodiments, a biomaterial is provided by graft polymerization of a polysaccharide and/or proteoglycan subunit to a biocompatible polymer followed by covalent linking of the peptide and/or protein subunit to the polysaccharide and/or proteoglycan subunit (see, e.g., FIG. 1).

Other coupling methods that may be used to join polysaccharide and/or proteoglycan subunits include, but are not limited to, an epoxide method, a tresyl chloride method and a method using sodium periodate (Clark et al., U.S. Pat. No. 5,677,276; Malson, U.S. Pat. No. 4,963,666). Peptides and/or protein subunits may also be conjugated to polysaccharides and/or proteoglycan subunits through multifunctional epoxides. For example, a bifunctional epoxide such as 1,4 butanediol diglycidyl ether (BDDE), may be used a cross-linking and a coupling agent. Examples of other multifunctional epoxides include, but are not limited to, polyglycerolpolyglycidyl ether (PGPGE), pentaerythriolpolyglycidyl ether (PEPGE) and diglycerolpolyglycidyl ether (DGPGE).

In a first step, the epoxide, such as BDDE, is added to a solution of a polysaccharide and/or proteoglycan subunit in excess and the reaction is allowed to proceed. Epoxides can react with from one to four of the hydroxyl groups on the sugar rings to form from one to four ether linkages. Alternatively, or in addition to forming ethers with hydroxyl groups, epoxides can form esters with carboxylic acids of a polysaccharide and/or proteoglycan subunit. Reaction of both epoxides of BDDE with functional groups of a single polysaccharide and/or proteoglycan subunit, results in cross linking. Where only one epoxide has reacted with the polysaccharide and/or proteoglycan subunit a free epoxide remains available for coupling to the peptide and/or protein subunit. After removing excess BDDE from the reaction solution, a peptide and/or protein subunit is added to the solution and covalently coupled to the polysaccharide and/or proteoglycan subunit.

Interpenetrating polymer networks may be formed either sequentially or simultaneously, by methods known to the skilled artisan. The proteoglycan, e.g. heparin sulfate and the peptide, e.g., GRGDSPS (SEQ ID NO: 21) may be linked using Schiff base chemistry or active ester (e.g., carbodiimide) chemistry. An interpenetrating polymer network of the above bioactive polymer may be formed with a biocompatible polymer, (e.g., a copolymer of butyl methacrylate and PEG) by using the method of Barber et al., *J Biomed. Mater. Res.* 2003, 38-47. Alternatively, during polymerization of a biocompatible polymer, e.g., butyl methacrylate, the desired proteoglycans e.g., heparin sulfate and peptide, e.g., Peptite 2000, are suspended in the reaction mixture to provide an interpenetrating polymer network. Interpenetrating polymer networks may also be made by conventional methods known to those of skill in the art such as chemical crosslinking (Kosmala et al., *Biomaterials* 2000, 21, 2019-2023) and free radical polymerization including photopolymerization (Barber et al., *J Biomed. Mater. Res.* 2003, 54, 38-47; Elisseff et al., *Plast. Reconstr. Surg.* 1999, 104, 1014-1022; Hasciri et al., *Biomed. Mater. Eng.* 2000, 10, 19-29; Song et al., *Electrophoresis* 2001, 22, 3688-3698; Elisseff et al., *J Biomed. Mater. Res.* 2000, 51, 164-171). For example, during polymerization of a biocompatible polymer, e.g., butyl methacrylate, the desired proteoglycan e.g., heparin sulfate and peptide, e.g., Peptite 2000, are suspended in the reaction mixture to provide an interpenetrating polymer network. Interpenetrating polymer networks may also be prepared by methods including melt blending, solution blending or other methods known to the skilled artisan.

A biocompatible polymer with a reactive group can provide for graft polymerization of a bioactive polymer to provide a biomaterial of the current invention. One preferred copolymer is a copolymer of butyl methacrylate and PEG containing a primary amine based on aminoethyl methacrylate. A preferred proteoglycan, e.g., heparan sulfate can be grafted to the biocompatible polymer, post copolymerization via, for example, carbodiimide chemistry. The peptide, e.g., an RGD peptide such as GRGDSP (SEQ ID NO: 15) can be grafted to PEG by any number of methods, e.g., using Schiff base chemistry and glutaraldehyde. Other methods include similar linking chemistries (e.g., carbodiimide, difunctional linkers like glutaraldehyde) with any hydroxy, amino, thio, isocyanate or other "active hydrogen" functional group polymer.

Acrylic copolymers may be synthesized using a variety of synthesis schemes. For example, copolymers can be formed using any of a number of polymerization techniques, including chain-growth polymerization techniques such as free-radical polymerization, cationic polymerization, anionic polymerization, Ziegler-Natta polymerization and metallocene polymerization.

Where block copolymers are formed, polymerization techniques known as "living radical polymerization" or "controlled radical polymerization" can be used. Examples include nitroxide-mediated polymerization (NMP), atom transfer radical polymerization (ATRP), and reversible addition-fragmentation chain transfer (RAFT) polymerization. Each of these techniques is well known.

For example, block copolymers containing polybutylacrylate have reportedly been synthesized using NMP, ATRP and RAFT polymerization (Tortosa et al., *Macromolecular Rapid Communications* 2001, 22, 957-961; Davis et al., *J. Polym. Sci., Part A: Polymer Chemistry* 2000, 38, 2274-2283; Beers et al., *Journal of Chemical Education* 2001, 78, 544; and Monteiro et al., *J. Polym. Sci., Part A: Polymer Chemistry* 2000, 38, 4206-4217).

As other examples, acrylate/methacrylate block copolymers have reportedly been synthesized by ATRP and RAFT polymerization (Shipp et al., *Am. Chem. Soc. Polym. Prep.* 1999, 40, 448; Chong et al., *Macromolecules*, 1999, 32, 2071-2074.

Another technique appropriate for block copolymer formation is sometimes referred to as a living cationic polymerization process. Typical cationic initiators for use in cationic polymerization embodiments of the present invention are generally of the Lewis acid type, for example, aluminum trichloride, boron trifluoride, boron trifluoride etherate complexes, titanium tetrachloride and the like. If desired, a cationic co-initiator can be added. Suitable cationic co-initiators include tertiary alkyl halides (e.g., t-butylchloride), tert-ester, tert-ether, tert-hydroxyl and tert-halogen containing compounds, such as cumyl esters of hydrocarbon acids, alkyl cumyl ethers, cumyl halides and cumyl hydroxyl compounds and hindered versions of the same. Also, electron pair donors such as dimethyl acetamide, dimethyl sulfoxide, or dimethyl phthalate can be added, as can proton-scavengers that scavenge water, such as 2,6-di-tert-butylpyridine, 4-methyl-2,6-di-tert-butylpyridine, 1,8-bis(dimethylamino)-naphthalene, or diusopropylethylamine amine. In one embodiment, the reaction is commenced by removing, a tert-ester, tert-ether, tert-hydroxyl or tert-halogen group from a co-initiator molecule by reacting it with the Lewis acid initiator in a suitable solvent system (e.g., a mixture of polar and non-polar solvents) in the presence of an electron pair donor. In place of the tert-leaving groups is a quasi-stable or "living" cation, which is stabilized by the surrounding tertiary carbons as well as the polar solvent system and election pair donors. A first monomer cationically propagates or polymerizes from each cation on the attached co-initiator molecule. Because the initiator complex is unstable, the monomer is commonly added to the reaction before the addition of the Lewis acid initiator. An additional monomer is subsequently added to form a block copolymer. In this connection, it is noted that a mono-functional initiator produces a diblock copolymer, a di-functional initiator attached to the surface is used to create a triblock copolymer, and so forth. The reaction can be terminated by adding a termination molecule such as methanol, water and the like. Further information can be found, for example, in U.S. Pat. Nos. 5,741,331 and 4,946,899, and U.S. patent application No. 20020107330.

The biomaterials of the current invention may form gels or semi-gels, which may be placed directly in a wound to facilitate healing. Growth factors may be used as peptide and/or protein subunits or may be added extraneously to biomaterials of the invention to further spur wound healing. In alternative embodiments, biomaterials of the invention can be coated on biodegradable meshes or other implanted materials, formed into sheets or other structures, or provided as stable solutions. Such biomaterials can be used on wounds such as, for example, chronic skin ulcers, burns, corneal wounds, incisions, etc. which involve body tissues being cut, abraded or otherwise damaged. Regeneration of tissue (e.g., cartilage, bone, nervous tissue, mussel tissue, soft tissue, vasculature, etc.) may also be enhanced by application of biomaterials of the invention. Furthermore, the gels can be used as an endoluminal paving in any vascular vessel and non-vascular vessel, e.g., esophagus, ureter, biliary vessel, etc.

The biomaterials of the invention may also be used as stent coatings with or without drug delivery, a bulk implant (e.g., vascular prosthesis), replacement for mucosal tissue (e.g., esophagus), coating on implants, coating on in vivo tubular structures, (e.g., blood vessels, gastrointestinal tract, urinary tract, etc.), an injectable or implantable bulking agent, an embolic agent for neurologic or blood borne applications (e.g., aneurysms, uterine fibroids, etc.), etc. The biomaterials of the invention may also be used as scaffolds for the production of tissue engineered constructs in vitro or in vivo.

The biomaterials of the invention may be tested in vitro, (i.e., cell culture using contact like endothelium or epithelial cells and non-contact cell lines like fibroblasts) and in vivo animal models such as subcutaneous implantation in guinea pigs (Polarek et al., *Wounds* 1994, 46; and Buckley et al., *PNAS USA* 1985, 7340); rat incisional models (Shah et al., *Lancet* 1992, 213); rabbit ear ulcer model (Pierce et al., *Amer. J. Path.* 1991, 629-646); rabbit knee femoral medial condyl defect (Von Schroeder et al., *J. Biomed. Mater. Res.* 1991, 329); full thickness wounds in guinea pigs (Cheng et al., *Arch. Dermatol.* 1988, 124:221-226); full thickness wounds in pigs (Welch et al., *J. Cell Biol.* 1990, 133-145); and pig burn model (Davis et al., *J. Surg Res.* 1990, 245-248). Those of skill in the art will understand that the results of such in vivo experiments are analyzed, for example, for enhanced tissue deposition, rate of epithelialization, cell type reactivity, growth factor delivery, etc. Other methods of assaying the biomaterials of the invention include, for example, vascular healing models (e.g., Tweden et al., *J. Heart Valve Dis.* 1995, 4, S90-97) vascular graft models (e.g., Greisler et al., *J. Vasc. Surg.* 1987, 393-399), endovascular paving models (e.g., Hem et al., *J Biomed. Mater. Res.* 1998, 266-76) and stent healing models (e.g., Vinnani et al., *Heart* 2003, 133-8.) Wound healing in non vascular applications can be assessed using a stent or paving methods in mucosal tissue in the esophagus, ureter or biliary structures.

EXAMPLES

The invention is further defined by reference to the following examples, which describe in detail methods for making and testing biomaterials of the invention. It will be apparent to those skilled in the art that many modifications, both to materials and methods, may be practiced without departing from the scope of the invention.

Example 1

Copolymerization of N-Butyl Methacrylate and Glycidyl Methacrylate

Prior to polymer formation, free radical inhibitors must be removed from N-butyl methacrylate and glycidyl methacrylate monomers. The monomer is placed in an addition funnel, secured above a column freshly packed with activated alumina (prepacked columns described in Aldrich Technical Bulletin AL-154 may also be used) and added drop wise to the column at a rate of addition sufficiently slow so that the column does not overflow. The monomer is then collected in an appropriate container.

Glycidyl methacrylate (3.65 grams), 2,2'-azobisisobutyronitrile (0.0125 grams), N-butyl methacrylate (14.2 grams) and tetrahydrofuran (100 mL) are mixed in a reaction vessel which is then sealed and evacuated under reduced pressure to remove oxygen. Nitrogen is then added to vessel and maintained at a constant rate of 2 psi while the reaction vessel is maintained at 60° C. for 48 hours. The polymer is precipitated using diethyl ether, dissolved again in THF and again precipitated using diethyl ether. The last two steps are repeated twice after which the polymer is dried in a vacuum oven overnight at 50° C. The dried polymer is ground to a powder and stored in a glass jar in a laboratory refrigerator.

Example 2

Formation of Secondary Amines from Copolymer of N-Butyl Methacrylate and Glycidyl Methacrylate A slight molar excess (ca. 5%) of propylamine was added to the copolymer of Example 1 in a glass petri dish under a nitrogen atmosphere. The reaction was allowed to proceed for about 20 minutes and then the polymer was washed with acetone. The acetone wash was repeated an additional three times and the polymer was then dried under nitrogen.

Example 3

Attachment of Hyaluronic Acid to Poly(Butyl Methacrylate-co-Glycidyl) Methacrylate The polymer prepared in Example 2 was equilibrated in 0.05 M MES-buffer (11 mL) at a pH of 6.8 for 40 minutes in glass petri dish. Hyaluronic acid (HA) (10 mg) was treated with 1-ethyl-3-(3 -dimethylaminop- ropyl)-carbodiimide (EDC) (10 mg) and hydroxybenzotriazole (HOBT) (12 mg) in 0.05 M MEH-buffer (11 mL) at a pH of 4.8 for 2 hours in glass vial. (Ratio of EDC:HOBt:HA=1:1.2:1). The HA solution was added to the base polymer coating in glass petri dish and reacted overnight after which the polymer coating was washed 3 times for 24 hours with distilled water and dried overnight.

The peptide GGGRGDGGG which is made either by New England Peptide Co., Gardner Mass. or Biopeptide Co., LLC, San Diego, Calif. is dissolved in a water-miscible solvent. The peptide solution is then dissolved in conjugation buffer (0.1 M MES buffer at pH of 4.7 2-20 mg per 2 mL) and is added to the polymer prepared in Example 3. Conjugation buffer (0.5 mL) is added to EDC and the EDC solution is added to the above reaction mixture (EDC to peptide ratio=1:1). The reaction mixture is shaken gently for three hours and the EDC solution removed. The polymer product is washed with distilled water three times.

Example 4

Demonstrating Attachment of Hyaluronic Acid to Poly(Butyl Methacrylate-co-Glycidyl) Methacrylate by Fluorophores-Assisted Carbohydrate Electrophoresis (FACE)

FACE analysis consists of three major steps: preparation of FACE standards, preparation of hyaluronan standards and samples and preparation and running of SDS gels.

Standards disaccharides (lyophilized powder) were reconstituted in ultra pure water at a concentration according to manufacturer directions and each standard was divided into five aliquots. The aliquots were frozen at −80° C. for 20 minutes and then lyophilized. The first aliquot was left at −80° C. to be directly lyophilized. The second aliquot was resuspended in 17.5 mM mercuric acetate and 50 mM sodium acetate (pH 5.0) and incubated for 30 minutes at room temperature. Then 30 μL of 50% AG 50W-X8 resin slurry was added to remove mercuric acetate and the solution was filtered through glass wool, frozen at −80° C. for 20 minutes and then lyophilized. The last three aliquots were resuspended in 100 μL of 0.0005% phenol red and 100 mM sodium acetate (pH 7.0). Then, 1.6 μL chondro-4-sulfatase (100 mU/mL) was added and the mixture was incubated at 37° C. for one hour, frozen at −80° C. for 20 minutes and then lyophilized. Then 20 μL of 100 mM ammonium acetate (pH 7.0) was added to each aliquot and followed by vortexing and spinning. The samples were toyed at −80° C. until used.

The sample (4 μL) is thawed, combined with 2 μL of 2-aminoacridone, vortexed and spun. Addition of sodium cyanoborohydride (4 μL) to the mixture, followed by incubation overnight at 37° C. provided FACE standards ladder ready for gel loading.

Hyaluronan standards were prepared as follows. Hyaluronan (1.2 mg) was dissolved in 1 mL of distilled water and periodically vortexed over a thirty minute period. The solution was divided into three different concentrations (ratio of 1:2:20) which were frozen at −80° C. for twenty minutes and then lyophilized. Each sample was resuspended in 35 μL of 100 mM ammonium acetate and 0.6 μL 0.1% acetic acid and 1.6 μL hyaluronanidase was added followed by incubation at 37° C. for one hour with vortexing and spinning at every twenty minute interval. 1.6 μL chondrotinase ABC was added followed by incubation at 37° C. for two hours with vortexing and spinning at every twenty minute interval. The samples were then heated at 100° C. for ten minutes, cooled on ice for ten minutes and stored at −80° C. until used.

The sample (8 μL) is thawed, combined with 4 μL of 2-aminoacridone, vortexed and spun. Addition of sodium cyanoborohydride (4 μL) to the mixture, followed by incubation overnight at 37° C. provided hyaluronan standards ready for gel loading.

Three different methods for attaching hyaluronic acid to the polymer prepared via the method of Example 2 were used. Sample A was prepared as described in Example 3 except that twice the amount of EDC was used. Sample B was prepared as described in Example 3. Sample C was prepared as described in Example 3 except that the starting polymer was equilibrated at pH 4.8 prior to addition of EDC.

Polymer samples for gel electrophoresis were prepared by crushing about 130 mg of polymer, adding 700 μL ammonium acetate, 12 μL 1% acetic acid, and 32 μL hyaluronadase. The samples were incubated at 37° C. for one hour with vortexing and spinning every twenty minutes. 32 μL chondrotinase ABC was added followed by incubation at 37° C. for two hours with vortexing and spinning at every twenty minute interval. The samples were then heated at 100° C. for ten minutes, cooled on ice for ten minutes and stored at −80° C. until used.

Electrophoresis samples were prepared as follows: 1 μL of a polymer sample was mixed with 4 μL of 1-aminoacridone while 4 μL of a hyaluronan sample was mixed with 1 μL of 1-aminoacridone. Glycerol (2.9 μL, 20%) was added to all samples loaded onto a gel, which were vortexed and spun twice before loading. The samples (5 μL) were loaded on a conventional SDS acrylamide gel with both resolving gel and stacking gel components.

Figure 2:
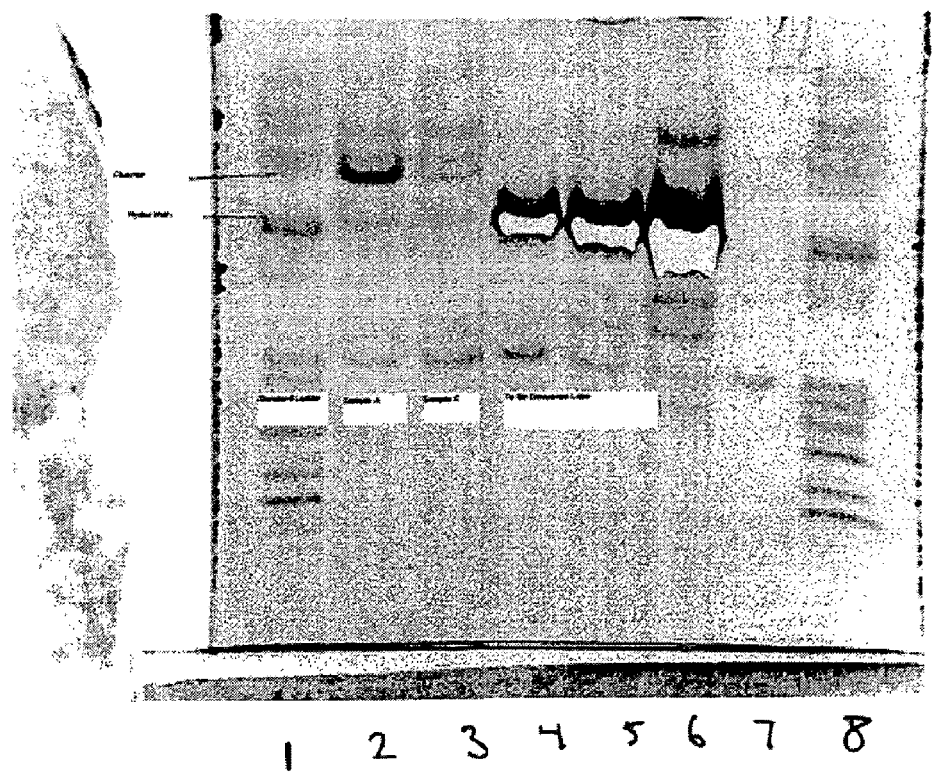
FIG. 2 is an SDS gel which demonstrates attachment of hyaluronic acid to the polymer prepared in Example 2. Lanes 1 and 8 are standards while lanes 2, 3 and 4 are hyaluronic acid attached to poly(butyl methacrylate-co-glycidyl methacrylate samples. Lanes 5, 6 and 7 are the hyaluronan standards.

An example of an SDS gel that demonstrates attachment of hyaluronon to a polymer is shown in FIG. 2. Lanes 1 and 8 are standards while lanes 2, 3 and 4 are hyaluronic acid attached to poly(butyl methacrylate-co-glycidyl methacrylate samples. Lanes 5, 6 and 7 are the hyaluronan standards.

Finally, it should be noted that there are alternative ways of implementing the present invention. For example, different combinations of building blocks may be used in the biomaterials of the invention or alternative synthetic methods may be used to make the biomaterials of the inventions. Accordingly, the present embodiments are to be considered as illustrative and not restrictive, and the invention is not to be limited to the details given herein, but may be modified within the scope and equivalents of the appended claims. All references and patents identified herein are incorporated by reference in their entirety for all purposes.

What is claimed is:

1. A synthetic biomaterial comprising:
   a bioactive polymer comprised of at least one peptide and/or protein subunit and at least one polysaccharide and/or proteoglycan subunit; and
   a biocompatible polymer that is different from said bioactive polymer,
   wherein the peptide and/or protein subunit of the bioactive polymer is a cell adhesion peptide, wherein the cell adhesion peptide is dRGD peptide, a YIGSR peptide (SEQ ID NO: 16) or a IVKAV peptide (SEQ ID NO: 20), and the at least one peptide and/or protein subunit is covalently bonded to the at least one polysaccharide and/or proteoglycan subunit, and wherein the biocompatible polymer and the bioactive polymer are a miscible polymer blend.

2. A synthetic biomaterial comprising:
   a bioactive polymer comprised of at least one peptide and/or protein subunit and at least one polysaccharide and/or proteoglycan subunit; and
   a biocompatible polymer,
   wherein the peptide and/or protein subunit of the bioactive polymer is a cell adhesion peptide and wherein the cell adhesion peptide is dRGD peptide, a YIGSR peptide (SEQ ID NO: 16) or a IVKAV peptide (SEQ ID NO: 20), and the at least one peptide and/or protein subunit is covalently bonded to the at least one polysaccharide and/or proteoglycan subunit and wherein the biocompatible polymer and the bioactive polymer are an immiscible polymer blend.

3. A synthetic biomaterial comprising:
a bioactive polymer comprised of at least one peptide and/or protein subunit and at least one polysaccharide and/or proteoglycan subunit; and
a biocompatible polymer that is different from said bioactive polymer;
wherein the bioactive polymer and the biocompatible polymer are crosslinked, and the at least one peptide and/or protein subunit is covalently bonded to the at least one polysaccharide and/or proteoglycan subunit.

4. A synthetic biomaterial comprising a graft polymer of:
a bioactive polymer comprising a polysaccharide and/or proteoglycan subunit and a peptide and/or protein subunit;
a biocompatible polymer that is different from said bioactive polymer;
wherein the polysaccharide and/or proteoglycan subunit is covalently bonded to the biocompatible polymer.

5. A synthetic biomaterial comprising:
a bioactive polymer consisting of at least one peptide and/or protein subunit and at least one polysaccharide and/or proteoglycan subunit; and
a biocompatible polymer that is different from said bioactive polymer, wherein the peptide and/or protein subunit of the bioactive polymer is a cell adhesion peptide and wherein the cell adhesion peptide is a dRGD peptide, YIGSR peptide (SEQ ID NO: 16) or a IVKAV peptide (SEQ ID NO: 20), and the at least peptide and/or protein subunit is covalently bonded to the at least one polysaccharide and/or proteoglycan subunit, and wherein the biocompatible polymer and the bioactive polymer are a miscible polymer blend.

6. A synthetic biomaterial comprising:
a bioactive polymer consisting of at least one peptide and/or protein subunit and at least one polysaccharide and/or proteoglycan subunit; and
a biocompatible polymer that is different from said bioactive polymer;
wherein the bioactive polymer and the biocompatible polymer are crosslinked, and the at least one peptide and/or protein subunit is covalently bonded to the at least one polysaccharide and/or proteoglycan subunit.

7. A synthetic biomaterial comprising a graft polymer of:
a bioactive polymer consisting of a polysaccharide and/or proteoglycan subunit and a peptide and/or protein subunit; and
a biocompatible polymer that is different from said bioactive polymer;
wherein the polysaccharide and/or proteoglycan subunit is covalently bonded to the biocompatible polymer.

8. A synthetic biomaterial comprising:
a bioactive polymer comprised of at least one peptide and/or protein subunit and at least one polysaccharide and/or proteoglycan subunit; and
a biocompatible polymer,
wherein the peptide and/or protein subunit of the bioactive polymer is a cell adhesion peptide and wherein the cell adhesion peptide is a RGD peptide, a dRGD peptide, a YIGSR peptide (SEQ ID NO: 16) or a IVKAV peptide (SEQ ID NO: 20), and the at least one peptide and/or protein subunit is covalently bonded to the at least one polysaccharide and/or proteoglycan subunit, and wherein the biocompatible polymer and the bioactive polymer are an immiscible polymer blend.

9. The biomaterial of claim 3, wherein the biocompatible polymer is polystyrene-isobutylene-polystyrene, a polyurethane, an ethylene vinyl acetate copolymer, a polyolefin elastomer, a polyamide elastomer, or homopolymer or copolymer comprising a monomer such as isobutylene, butyl acrylate, butyl methacrylate, and combinations thereof.

10. The biomaterial of claim 4, wherein the biocompatible polymer is polystyrene-isobutylene-polystyrene, a polyurethane, an ethylene vinyl acetate copolymer, a polyolefin elastomer, a polyamide elastomer, or homopolymer or copolymer comprising a monomer such as isobutylene, butyl acrylate, butyl methacrylate, and combinations thereof.

11. The biomaterial of claim 6, wherein the biocompatible polymer is polystyrene-isobutylene-polystyrene, a polyurethane, an ethylene vinyl acetate copolymer, a polyolefin elastomer, a polyamide elastomer, or homopolymer or copolymer comprising a monomer such as isobutylene, butyl acrylate, butyl methacrylate, and combinations thereof.

12. The biomaterial of claim 7, wherein the biocompatible polymer is polystyrene-isobutylene-polystyrene, a polyurethane, an ethylene vinyl acetate copolymer, a polyolefin elastomer, a polyamide elastomer, or homopolymer or copolymer comprising a monomer such as isobutylene, butyl acrylate, butyl methacrylate, and combinations thereof.

\* \* \* \* \*

UNITED STATES PATENT AND TRADEMARK OFFICE
CERTIFICATE OF CORRECTION

PATENT NO.       : 7,709,439 B2                                              Page 1 of 1
APPLICATION NO.  : 10/781932
DATED            : May 4, 2010
INVENTOR(S)      : Michael N. Helmus et al.

It is certified that error appears in the above-identified patent and that said Letters Patent is hereby corrected as shown below:

Specification, col. 3, line 16, after "protein", change "portion," to --portion.--
    Specification, col. 4, line 42, after "or", change "polyomithine" to --polyornithine--.
    Specification, col. 12, line 41, after "or", change "diusopropylethylamine" to --diisopropylethylamine--.
    Specification, col. 14, line 38 after "1-ethyl-3-", change "(3 -dimethylaminop- ropyl)-carbodiimide" to --(3-dimethylaminopropyl)-carbodiimide--.
    Specification, col. 15, line 19, after "were", change "toyed" to --stored--.

Signed and Sealed this

Twenty-eighth Day of September, 2010

David J. Kappos
*Director of the United States Patent and Trademark Office*